United States Patent [19]

Mills

[11] 4,167,569

[45] Sep. 11, 1979

[54] PYRIMIDO[1,2-a]BENZIMIDAZOLE DERIVATIVES

[75] Inventor: Stuart D. Mills, Macclesfield, England

[73] Assignee: Imperial Chemical Industries Limited, London, England

[21] Appl. No.: 855,003

[22] Filed: Nov. 23, 1977

[30] Foreign Application Priority Data

Dec. 9, 1976 [GB] United Kingdom ............... 51426/76
Aug. 9, 1977 [GB] United Kingdom ............... 33341/77

[51] Int. Cl.$^2$ ................. C07D 487/04; C07D 491/14; A61K 31/505
[52] U.S. Cl. .................................... 424/251; 544/247; 544/250; 548/306
[58] Field of Search ................. 260/256.4 F, 256.5 R; 544/247, 250; 424/251

[56] References Cited

U.S. PATENT DOCUMENTS

| | | | |
|---|---|---|---|
| 3,468,888 | 9/1969 | Chow | 260/256.4 |
| 3,988,340 | 10/1976 | Partyka et al. | 260/256.4 F |
| 4,109,087 | 8/1978 | Denzel et al. | 544/250 |
| 4,109,091 | 8/1978 | Denzel et al. | 544/250 |

OTHER PUBLICATIONS

Chow et al., Chem. Abs. 78, 111242k (1973).

*Primary Examiner*—Mark L. Berch
*Attorney, Agent, or Firm*—Cushman, Darby & Cushman

[57] ABSTRACT

The invention concerns 3,4-dihydropyrimido [1,2-a]benzimidazole derivatives bearing one or more substituents at positions 6, 7, 8 or 9; processes for their preparation and manufacture; and pharmaceutical compositions thereof. The compounds inhibit the aggregation of blood-platelets and may be used in vivo, in the treatment or prophylaxis of thrombosis or occlusive vascular disease, or in vitro, in helping to stabilize preparations of blood platelets. Representative compounds of the invention are 7- and 8- acetyl-3,4-dihydropyrimido[1,2-a]benzimidazol-2(1H)-one.

15 Claims, No Drawings

PYRIMIDO[1,2-a]BENZIMIDAZOLE DERIVATIVES

This invention relates to benzimidazole derivatives and more particularly it relates to pyrimido[1,2-a]benzimidazole derivatives which inhibit the aggregation of blood platelets.

According to the invention there is provided a pyrimido[1,2-a]benzimidazole derivative of the formula:

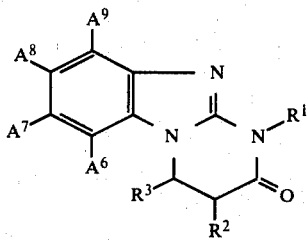

wherein $R^1$ is hydrogen, or a $C_{1-6}$-alkyl radical; $R^2$ and $R^3$, which may be the same or different, are hydrogen or $C_{1-6}$-alkyl radicals; one, two or three of $A^6$, $A^7$, $A^8$ and $A^9$, which may be the same or different, are halogen atoms, $C_{1-6}$-alkyl, $C_{1-6}$-alkoxy, $C_{2-6}$-alkanoyl, 1-(hydroxy)-$C_{1-6}$-alkyl, $C_{1-6}$-alkylthio, $C_{1-6}$-alkylsulphinyl or cyano radicals, or benzoyl radicals optionally substituted by a halogen atom, a $C_{1-6}$-alkoxy or $C_{1-6}$-alkyl radical, and the remainder of $A^6$, $A^7$, $A^8$ and $A^9$ are hydrogen; or an adjacent pair of $A^6$, $A^7$, $A^8$ and $A^9$ together constitute a $C_{1-6}$-alkylenedioxy diradical, another of $A^6$, $A^7$, $A^8$ and $A^9$ is hydrogen, or is an atom or radical as defined above, and the remaining one of $A^6$, $A^7$, $A^8$ and $A^9$ is hydrogen; provided that when only one of $A^6$, $A^7$, $A^8$ and $A^9$ is a halogen atom, $C_{1-6}$-alkyl or $C_{1-6}$-alkoxy radical at least one of the remainder of $A^6$, $A^7$, $A^8$ and $A^9$ is other than hydrogen.

It will be observed that the compounds of formula I are derivatives of 3,4-dihydropyrimido[1,2-a]benzimidazol-2(1H)-one, which ring system will be numbered throughout this specification as shown, by way of example only, in the following formula:

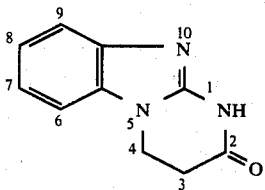

It will be observed that compounds of formula I wherein $R^1$ is hydrogen can exist in different tautormeric forms, one of which is depicted in formula II. It is to be understood that the structural designations and nomenclature used herein relate to the most probable and predominant tautomeric form, but that the invention embraces compounds of formula I wherein $R^1$ is hydrogen which are in any tautomeric form or a mixture of such forms.

It will further be observed that, depending on the nature of the substituents $R^2$ and $R^3$ and the substituents $A^6$, $A^7$, $A^8$ and $A^9$, a compound of formula I may contain one or more asymmetric carbon atoms, and may therefore be isolated in racemic forms or optically active forms. This specification is addressed to any racemic or optionally active form of a compound of formula I which possesses the above useful properties; it being a matter of common knowledge how to obtain an optically active form, for example by resolution of a racemic form, or by synthesis from an optically active starting material, and how to determine the biological properties of the optical isomers by the test described hereinbelow.

A particular value for any one of $R^1$, $R^2$ and $R^3$, when it is a $C_{1-6}$-alkyl radical, is, for example, a methyl or ethyl radical.

By way of example only, particular values for any one of $A^6$, $A^7$, $A^8$ and $A^9$ are:

when it is a halogen atom, a fluorine, chlorine or bromine atom;

when it is a $C_{1-6}$-alkyl radical, a methyl, ethyl or propyl radical;

when it is a $C_{1-6}$-alkoxy radical, a methoxy, ethoxy or i-propoxy radical;

when it is a $C_{2-6}$-alkanoyl radical, an acetyl, propionyl or butyryl radical;

when it is a 1-(hydroxy)-$C_{1-6}$-alkyl radical, a hydroxymethyl or 1-(hydroxy)-$C_{2-6}$-alkyl radical, for example a 1-hydroxyethyl, 1-hydroxypropyl or 1-hydroxybutyl radical;

when it is a $C_{1-6}$-alkylthio radical, a methylthio or ethylthio radical;

and when it is a $C_{1-6}$-alkylsulphinyl radical, a methylsulphinyl or ethylsulphinyl radical.

Particular values for specific substituents which may be present on the benzene ring of a benzoyl radical when any one of $A^6$, $A^7$, $A^8$ and $A^9$ is such a radical, are by way of example only:

for a halogen atom, a fluorine, chlorine or bromine atom;

for a $C_{1-6}$-alkyl radical, a methyl radical;

and for a $C_{1-6}$-alkoxy radical, a methoxy radical.

A particular value for a $C_{1-6}$-alkylenedioxy diradical when an adjacent pair of $A^6$, $A^7$, $A^8$ and $A^9$ constitute such a radical is, for example a methylenedioxy or isopropylidenedioxy diradical.

Particularly suitable arrangements of substituents $A^6$, $A^7$, $A^8$ and $A^9$ are, for example, when two thereof are $C_{1-6}$-alkyl or $C_{1-6}$-alkoxy radicals, or a $C_{1-6}$-alkyl radical and a halogen atom, or halogen atoms, or constitute a $C_{1-6}$-alkylenedioxy diradical, and the remainder thereof, are hydrogen; or when one thereof is a $C_{2-6}$-alkanoyl, 1-(hydroxy)-$C_{1-6}$-alkyl, $C_{1-6}$-alkylthio, $C_{1-6}$-alkylsulphinyl or cyano radical, or a benzoyl radical optionally substituted as defined hereinabove, and the remainder thereof are hydrogen.

Specific suitable arrangements of radicals $A^6$, $A^7$, $A^8$ and $A^9$ are, for example, when two thereof constitute a 6,7-7,8-, 8,9- or 6,9-dimethyl radical, a 7,8-dichloro, 7-chloro-8-methyl, 7-methyl-8-chloro, 7,8-dimethoxy, 7,8-diisopropoxy or a 7,8-methylenedioxy diradical, and the remainder thereof are hydrogen; or when one thereof is a 7- or 8-acetyl, -butyryl, -benzoyl, -(p-chloro)benzoyl, -methylthio, -ethylthio, -ethylsulphinyl, -cyano or -[1-(hydroxy)ethyl] radical, and the remainder thereof are hydrogen.

It will be appreciated that various particular and individual compounds of the invention are comprised within the above general definition, namely those compounds of formula I, wherein one of the radicals $R^1$, $R^2$, $R^3$, $A^6$, $A^7$, $A^8$ and $A^9$ has one of the above defined particular or specific values, and the remainder of the said radicals have any of the defined general, particular or specific values. However, specific groups of compounds of formula I which are of particular interest comprise those compounds of formula I wherein:
(i) $R^1$ is hydrogen;
(ii) $R^1$ is a $C_{1-6}$-alkyl radical, and in particular a methyl or ethyl radical;
(iii) $R^1$, $R^2$ and $R^3$ are all hydrogen;
(iv) one of $A^6$, $A^7$, $A^8$ and $A^9$ is a halogen atom, or a $C_{1-6}$-alkyl or $C_{1-6}$-alkoxy radical; another one or two of $A^6$, $A^7$, $A^8$ and $A^9$ is a halogen atom, or a $C_{1-6}$-alkyl, $C_{1-6}$-alkoxy, $C_{2-6}$-alkanoyl, 1-(hydroxy)-$C_{1-6}$-alkyl, $C_{1-6}$-alkylthio, $C_{1-6}$-alkylsulphinyl or cyano radical, or a benzoyl radical optionally substituted as defined hereinbefore; or another adjacent pair of $A^6$, $A^7$, $A^8$ and $A^9$ together constitute a $C_{1-6}$-alkylenedioxy diradical; and the remainder of $A^6$, $A^7$, $A^8$ and $A^9$ are hydrogen;
(v) one, two or three of $A^6$, $A^7$, $A^8$ and $A^9$ are $C_{2-6}$-alkanoyl, 1-(hydroxy)-$C_{1-6}$-alkyl, $C_{1-6}$-alkylthio, $C_{1-6}$-alkylsulphinyl or cyano radicals, or benzoyl radicals optionally substituted as defined hereinabove; or an adjacent pair of $A^6$, $A^7$, $A^8$ and $A^9$ together, constitute a $C_{1-6}$-alkylenedioxy diradical; and the remainder of $A^6$, $A^7$, $A^8$ and $A^9$ are hydrogen;
and in each case the remainder of $A^6$, $A^7$, $A^8$, $A^9$, $R^1$, $R^2$ and $R^3$ have any of the above general, particular or specific values.

Yet further specific groups of compounds of the invention which are particularly preferred comprise those compounds of formula I wherein:
(a) $R^1$ is hydrogen, $R^2$ and $R^3$, which may be the same or different, are hydrogen or methyl radicals, at least two of $A^6$, $A^7$, $A^8$ and $A^9$ are hydrogen, and the remainder of $A^6$, $A^7$, $A^8$ and $A^9$ have any of the above defined values other than hydrogen;
(b) $R^1$, $R^2$ and $R^3$ have the meanings defined in (a) immediately above, $A^7$ and one of $A^6$, $A^8$ and $A^9$ have any of the above defined values other than hydrogen, and the remainder of $A^6$, $A^8$ and $A^9$ are hydrogen;
(c) $R^1$, $R^2$ and $R^3$ have the meanings defined in (a) immediately above, $A^8$ and one of $A^6$, $A^7$ and $A^9$ have any of the above defined values other than hydrogen, and the remainder of $A^6$, $A^7$ and $A^9$ are hydrogen;
(d) $R^1$, $R^2$ and $R^3$ have the meanings defined in (a) immediately above, $A^7$ and/or $A^8$ have any of the above defined values other than hydrogen, and the remainder of $A^6$, $A^7$, $A^8$ and $A^9$ are hydrogen.

Still further groups of preferred compounds comprise those compounds defined in any of the above groups (a)-(d) wherein in addition:
(i) $A^7$ or $A^8$ is a cyano, acetyl, 1-(hydroxy)ethyl or benzoyl radical; or
(ii) $A^7$ and $A^8$ together constitute a methylenedioxy diradical or are both methoxy, ethoxy or isopropoxy radicals.

Particular compounds of the invention are described in the accompanying Examples, but specific compounds which are preferred are 7- and 8-acetyl-, 7- and 8-benzoyl-, 7- and 8-cyano-, 7,8-diisopropoxy- and 7,8-methylenedioxy-3,4-dihydropyrimido[1,2-a]benzimidazol-2(1H)-one, and 7- and 8-benzoyl-4-methyl-3,4-dihydropyrimido[1,2-a]benzimidazol-2(1H)-one.

The compounds of the invention may be obtained by any known general procedure for the synthesis of analogous compounds. Such procedures are illustrated by the following in which $R^1$, $R^2$, $R^3$, $A^6$, $A^7$, $A^8$ and $A^9$ have any of the meanings defined above:

(a) Reacting a 2-amino-benzimidazole of the formula:

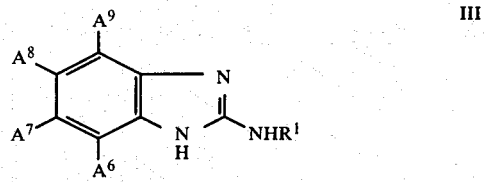

with an ethylenic acid derivative of the formula:

$$R^3-CH=CR^2-CO-Z \qquad IV$$

wherein Z is a halogen atom, for example a chlorine or bromine atom, or Z is a $C_{1-4}$-alkoxy radical, for example a methoxy or ethoxy radical.

The reaction may be carried out in an inert solvent or diluent, for example methanol, ethanol, acetone, tetrahydrofuran or acetonitrile, and may be accelerated by heating, for example, to the reflux temperature of the reaction mixture. The reaction is preferably carried out however, at a temperature of, for example 15° to 80° C.

When a compound of formula IV wherein Z is a halogen atom is used, a suitable base, for example a tertiary amine, for example triethylamine, may also conveniently be present.

The starting materials of formula III may be obtained by standard methods used in benzimidazole chemistry. Thus when $R^1$ is hydrogen, the starting materials may be made by analogy to 2-aminobenzimidazole, for example by reaction of a 1,2-diaminobenzene of the formula:

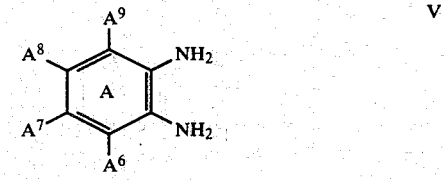

with cyanamide, or cyanogen bromide or chloride, optionally in the presence of base. When $R^1$ is an alkyl radical, the starting materials may be obtained by analogy with 2-methylaminobenzimidazole, for example, by reaction of an alkylamine with a 2-bromo- or 2-chlorobenzimidazole, itself conveniently obtained, for example, by reaction of a compound of formula V with urea, followed by conventional halogenation with phosphorus oxybromide or oxychloride. Alternatively when $R^1$ is an alkyl radical, the starting materials of formula III may be made by reaction of a compound of formula V with the appropriate N-alkyl cyanamide in the presence of base.

It will be appreciated that when benzene ring A is asymmetrically substituted the process (a) generally gives rise to a mixture of positional isomers. These isomers may be separated by conventional procedures of organic chemistry, for example by fractional crystallisation from a suitable solvent.

(b) Cyclising a compound of the formula:

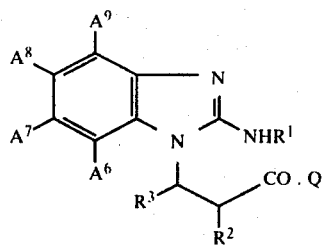

VI methanol, and at a temperature in the range, for example, 50°–250° C.

When Q is a hydroxy radical the cyclisation may also be carried out in the presence of a dehydrating agent, for example a strong mineral acid, for example polyphosphoric acid, or a carbodiimide, for example dicyclohexylcarbodiimide, and conveniently in the presence of a suitable solvent or diluent, for example in the case of a carbodiimide, chloroform, and at a temperature in the range, for example, 15°–100° C.

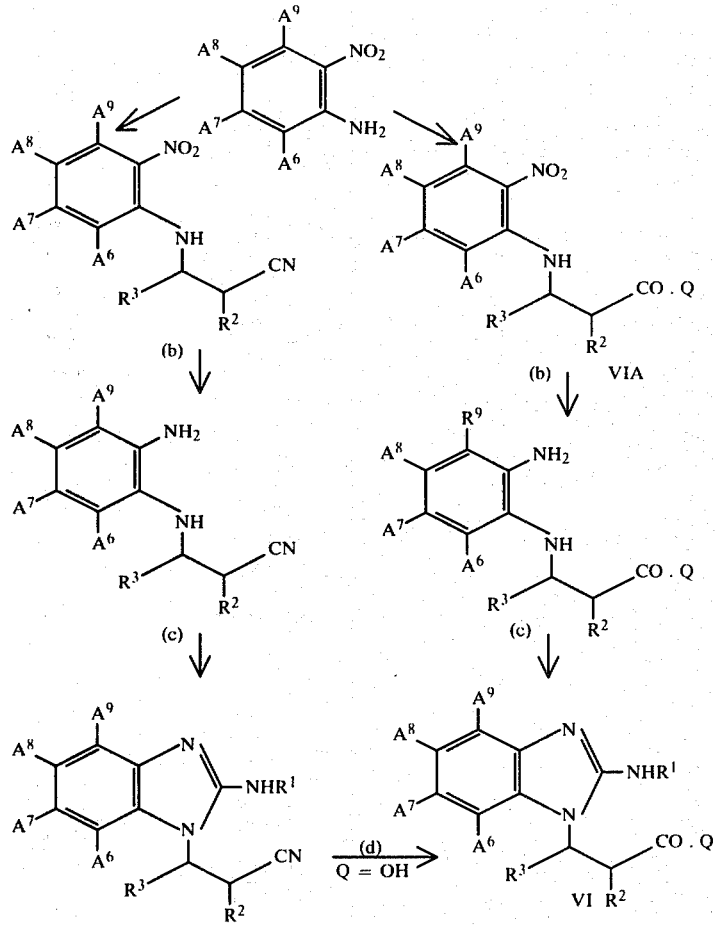

Scheme 1

Reagents:-
(a)-base, e.g. quaternary ammonium hydroxide.

(b)-hydrogen, palladium-on-charcoal.

(c)-Cn . Br (for $R^1$ = H) or alkylcyanamide (for $R^1$ = alkyl); then strong base e.g. NaOH.

(d)-aqueous strong base e.g. NaOH.

wherein Q is a hydroxy or $C_{1-4}$-alkoxy radical.

The cyclisation is preferably carried out thermally by heating a compound of formula VI at a temperature in the range, for example 50°–250° C. An inert solvent or diluent, for example, ethanol, dimethylformamide or diphenyl ether, may conveniently be present.

When Q is a $C_{1-4}$-alkoxy radical the reaction may also conveniently be carried out in the presence of a base, for example sodium ethoxide or methoxide, preferably in a suitable solvent or diluent, for example ethanol or The starting materials of formula VI may be obtained by conventional procedures, for example as described in the accompanying Examples, and as shown in Scheme 1, starting with an appropriately substituted o-nitroaniline. Alternatively and conveniently, an appropriately substituted o-nitro-chloro- or bromo-benzene may be reacted with a 3-aminopropionic acid of the formula:

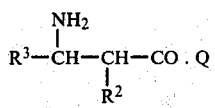

wherein Q has the meaning defined above, conveniently at a temperature in the range 50°–150° C., and preferably in a solvent or diluent, for example 2-methoxyethanol, and in the presence of an acid acceptor, for example sodium hydrogen carbonate. An intermediate of the formula:

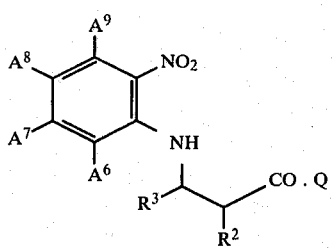

is thereby obtained which can be employed in the above Scheme 1. The starting materials of formula VI may conveniently be prepared and used in situ in process (b) without their separate isolation and purification.

A particular advantage of process (b) is that, unlike process (a) hereinabove, it does not give rise to positional isomers when the benzene ring of the benzimidazole moiety of a compound of formula VI is asymmetrically substituted.

(c) For a compound of formula I wherein at least one of $A^6$, $A^7$, $A^8$ and $A^9$ is a 1-(hydroxy)-$C_{1-6}$-alkyl radical, reducing a compound of formula I wherein at least one of $A^6$, $A^7$, $A^8$ and $A^9$ is a $C_{1-6}$-alkanoyl radical.

The reduction may be carried out by any known procedure compatible with the other radicals present, for example by reduction with a metal hydride, or a similar active hydride reagent.

Thus, the reduction may be carried out, for example, using an alkali metal borohydride, for example sodium or potassium borohydride, preferably in a suitable solvent, for example dimethyl formamide, and at a temperature in the range, for example, 10°–150° C.

The necessary starting materials may be obtained by the process described hereinbefore, or alternatively may be made by direct acylation or benzoylation of an appropriate compound of formula I using an acyl or benzoyl halide in the presence of a Friedel Craft catalyst.

(d) For a compound of formula I wherein at least one of $A^6$, $A^7$, $A^8$ and $A^9$ is a $C_{1-6}$-alkylsulphinyl radical, oxidising a compound of formula I wherein at least one of $A^6$, $A^7$, $A^8$ and $A^9$ is a $C_{1-6}$-alkylthio radical.

The oxidation may be carried out by any known procedure for the production of sulphoxides, for example using hydrogen peroxide, a peracid, for example peracetic acid, or an alkali metal periodate, for example sodium or potassium periodate. The oxidising agent is preferably not present in large excess and the reaction temperature is generally best kept in the range, for example, 5°–35° C., in order to minimise sulphone formation. An inert solvent or diluent, for example, water, acetic acid or aqueous ethanol, is preferably also used.

As stated above, the pyrimido[1,2-a]benzimidazole derivatives of formula I possess the property of inhibiting the aggregation of blood platelets. This property may be demonstrated in vitro by adding a test compound to a stirred sample of citrate treated human, platelet-rich plasma, and measuring the effect of the test compound in delaying or reducing the aggregation of blood platelets caused by the addition of collagen or adenosine 5'-diphosphate. In this test, compounds of formula I markedly inhibit the aggregation of blood platelets at concentrations of $10^{-4}$ molar or less.

Thus, by way of illustration only, an equimolar mixture of 7- and 8-acetyl-3,4-dihydropyrimido[1,2-a]benzimidazol-2(1H)-one shows significant inhibition at a concentration of $10^{-6}$ molar.

Blood platelets when stored for several hours and then infused into an animal or man tend to lose most of their haemostatic activity. Compounds which inhibit the aggregation of blood platelets in vitro are therefore useful in helping to stabilise preparations of blood platelets and thus to preserve their haemostatic activity in vivo. Such compounds may therefore usefully be added, for example, to whole blood for prolonged storage in blood-banks, to whole blood for circulation through isolated organs prior to their transplant or through heart-lung machines, and to suspensions of blood platelets prepared for use in the treatment of congenital or drug-induced thrombocytopenias.

The ability of compounds of formula I to inhibit the aggregation of blood platelets may also be demonstrated in vivo using standard tests in rats or mice in which thrombocytopenia has been produced. Thus for example a test compound is first dosed orally to rats and then, after several hours, adenosine 5'-diphosphate (ADP) (5 mg./kg.) is administered intravenously. After 15 seconds an arterial blood sample is taken and the blood platelet count is determined electronically using a Coulter counter. This count is then compared with the blood platelet count of an arterial blood sample taken immediately before the administration of the ADP. The administration of ADP produces a marked thromobocytopenia which is at its maximum after approximately 15 seconds. Compounds which inhibit this ADP-induced thrombocytopenia are considered to be active.

In a further standard test eight mice are dosed orally with a test compound. After 4 hours four of the mice are injected intravenously with a solution of collagen (1 mg./kg.) in a diluent, and the remaining mice are injected with diluent only, so that they serve as a control group. After 1 minute, arterial blood samples are taken from each mouse in each group, and the blood platelet counts determined by standard means. Again, compounds which inhibit this collagen-induced thrombocytopenia are considered active.

The in vivo activity of any specific compound of formula I necessarily varies according to its precise chemical structure but, in general, compounds of formula I show activity in one or both of the above in vivo tests at a dose of 100 mg./kg. or less, and without any overt toxicity or adverse effects being observed at the active dose. Thus, by way of illustration only, an equimolar mixture of 7- and 8-cyano-3,4-dihydropyrimido[1,2-a]benzimidazol-2(1H)-one showed significant activity at an oral dose of 25 and 50 mg./kg. respectively in ADP-induced and collagen-induced thrombocytopenia, without any evidence of toxicity or adverse effects being observed.

Compounds which inhibit the aggregation of blood platelets in vivo have been used in the treatment of prophylaxis of thrombosis or occlusive vascular disease.

When used in vivo, a compound of formula I is conveniently administered in the form of a pharmaceutical composition comprising a compound of formula I together with a pharmaceutically acceptable diluent or carrier. Such a composition is provided as a further feature of the invention and is, for example, conveniently in a form suitable for oral administration for example as a tablet, capsule, aqueous or oily suspension. Alternatively it may be in a form suitable for parenteral administration, for example, as a sterile injectable suspension.

Such compositions may be prepared by conventional methods using conventional excipients. A composition for oral administration should preferably contain from 50 mg. to 500 mg. per unit dose, and a composition for parenteral administration should preferably contain from 0.5 mg./ml. to 20 mg./ml. per unit dose; the more dilute compositions being useful for infusion rather than injection.

Compositions intended for use in the treatment or prophylaxis of thrombosis or occlusive vascular disease may also contain one or more agents which can have a beneficial effect on the disease or on associated conditions, for example ticlopidine, clofibrate, sulfinpyrazone, dipyridamole, acetyl salicylic acid or methyl 4-(aminoacetyl)phenoxyacetate.

When used to inhibit the aggregation of blood-platelets in warm blooded animals, a compound of formula I may be administered at a daily intravenous dose in the range 0.2 mg./kg. to 5 mg./kg. Alternatively a compound of formula I may be administered at a daily oral dose in the range 5 mg./kg. to 20 mg./kg. The doses may be given more conveniently in divided form. In man these doses are equivalent to a total daily dose of from 25 mg. to 350 mg. by the intravenous route, or of from 0.35 g. to 1.4 g. by the oral route.

The invention is illustrated by the following nonlimiting Examples in which:

(i) All evaporations are carried out by rotary evaporation under reduced pressure unless otherwise stated;

(ii) Unless otherwise stated, all operations were carried out at room temperature, that is at a temperature in the range 18°-25° C.;

(iii) NMR spectra, unless stated otherwise, are for protons and were performed at 100 MHz in hexadeutero-dimethylsulphoxide (d$_6$-DMSO) as solvent, using tetramethylsilane (TMS) as an internal standard;

(iv) TFA stands for trifluoroacetic acid; and (v) Yields, where given, are purely illustrative and are not to be construed as the maximum attainable.

EXAMPLES 1-3

Methyl acrylate (15 g.) was added to a solution of 2-amino-5,6-dimethylbenzimidazole (27.2 g.) in ethanol (100 ml.). After stirring for 2 days at room temperature, the crystalline precipitate which had formed in the reaction mixture was separated by filtration, washed with ethanol and then with ether, to give 7,8-dimethyl-3,4-dihydropyrimido[1,2-a]-benzimidazol-2(1H)-one (37.2 g.), m.p. 322°-323° C.

In a similar manner, but using the appropriate 2-aminobenzimidazole of the formula:

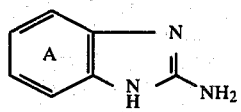

and methyl acrylate (MA), there were obtained the following compounds of the formula:

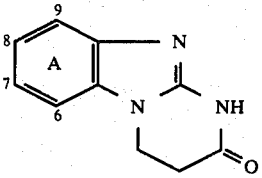

| Example No. | Starting Materials | | Substituents on ring A | Product IX | |
|---|---|---|---|---|---|
| | VIII (g.) | MA (g.) | | m.p.(°C.) | Yield (g.) |
| 2 | 0.9 | 0.5* | 6,9-dimethyl | 270-271 | 0.45 |
| 3 | 1.2 | 0.4 | 7,8-di-isopropoxy | 263-266 | 0.6 |

*reaction heated under reflux for 2 days in the absence of air, using a mixture of ethanol (10ml.) and methanol (2ml.) as solvent.

Those of the starting materials of formula VIII which are new were obtained as follows:

(a) 2-amino-4,7-dimethylbenzimidazole (for Example 2)

A mixture (70.0 g.) of p-xylene diamines (obtained by catalytic hydrogenation of the mixture of dinitro-p-xylenes formed on nitration of p-xylene) which contained approximately 60% of 3,6-dimethyl-1,2-diaminobenzene was converted to its monohydrochloride by addition of aqueous 2 N hydrochloric acid (270 ml.), followed by evaporation. A mixture of the monohydrochloride (86.2 g.) in water (120 ml.) was heated under reflux and a solution of cyanamide (23.1 g.) in water (50 ml.) was added to the boiling mixture during 20 minutes. After further heating under reflux for 1 hour, the reaction mixture was basified by addition of a solution of sodium hydroxide (20.8 g.) in water (50 ml.). The mixture obtained was then heated under reflux for 18 hours, and then cooled. The oil which formed, was separated by decantation and then triturated first with water (250 ml.) and then with chloroform (3×150 ml.). The residual tar was partly dissolved in acetone (150 ml.) and the solution obtained was purified by fractional chromatography on a column of silica gel (1.5 kg.) using first methanol-chloroform (1:1 v/v), and then methanol as eluant. Evaporation of the combined methanol fractions gave 2-amino-4,7-dimethyl-benzimidazole (13.9 g.) which was further purified by recrystallisation from ethanol to give pure material (6.1 g.), m.p. 164°-170° C.

(b) 2-amino-5,6-di-isopropoxybenzimidazole (for Example 3)

A solution of 1,2-diamino-4,5-di-isopropoxybenzene (2.24 g.) in methanol (40 ml.) was added to a mixture of cyanogen bromide (1.6 g.) in water (40 ml.). The mixture was stirred at 20°-25° C. for 70 hours and then basified by addition of an excess of aqueous ammonia solution (density 0.88). The mixture was then separated by filtration and the filtrate evaporated. The residue which was obtained was mixed with water (50 ml.) and chloroform (50 ml.). The chloroform phase was separated, dried (MgSO4) and evaporated. The residual gum obtained, was purified by chromatography on a column of silica gel (40 g.) using methanol-chloroform (1:3 v/v) as eluant, to give 2-amino-5,6-di-isopropoxybenzimidazole as a sticky solid (1.2 g.), having characteristic absorption bands at $\nu$ 3400, 3320, 3080, 1660 and 1565 cm$^{-1}$, in the infra-red (IR) spectrum.

EXAMPLES 4 AND 5

Using a similar procedure to that described in Example 1, there was obtained, from methyl acrylate (1.0 g.) and 2-amino-5-chloro-6-methylbenzimidazole (1.75 g.), a 1:1 mixture (0.8 g.) of 7-chloro-8-methyl-3,4-dihydropyrimido[1,2-a]-benzimidazol-2(1H)-one (Example 4) and 8-chloro-7-methyl-3,4-dihydropyrimido[1,2-a]benzimidazol-2(1H)-one (Example 5). The mixture had m.p. >314° C.

That the mixture was 1:1 was shown by the proton n.m.r. spectrum. The aromatic protons showed 4 signals $\delta$ 7.72(s), 7.59(s) and 7.60(s), 7.47(s) ppm in trifluoroacetic acid (TFA), relative to tetramethylsilane (TMS) as standard. The integration was the same for all the signals.

The 2-amino-5-chloro-6-methylbenzimidazole used as starting material was obtained in an analogous manner to that used for 2-amino-5,6-di-isopropoxybenzimidazole required for Example 3. Thus it was obtained as a solid (1.74 g.) m.p. 240°–247° C., from the reaction of cyanogen bromide (2.43 g.) with 4-chloro-5-methyl-1,2-diaminobenzene (2.4 g.).

EXAMPLES 6 AND 7

Using a similar procedure to that described in Example 1, there was obtained from methyl acrylate (0.77 g.) and 2-amino-5-methylthiobenzimidazole (1.45 g.) a 1:1 mixture (0.9 g.) of 7-methylthio-3,4-dihydropyrimido[1,2-a]benzimidazol-2(1H)-one (Example 6) and 8-methylthio-3,4-dihydropyrimido[1,2-a]-benzimidazol-2(1H)-one (Example 7). The mixture had m.p. 234°–238° C., and the C$_{13}$ NMR spectrum (d$_4$-acetic acid) showed 6 signals for the aromatic carbons at $\delta$ 108.9, 107.9, 116.0, 114.6 and 132.3, 130.9 ppm, relative to TMS as standard. The integration for each signal was the same.

The 2-amino-5-methylthiobenzimidazole used as starting material was obtained in analogous manner to that used for 2-amino-5,6-di-isopropoxybenzimidazole required for Example 3. Thus it was obtained as a solid (1.45 g.), m.p. 195°–210° C., sufficiently pure for further use, from the reaction of cyanogen bromide (2.06 g.) with 4-methylthio-1,2-diaminobenzene (2 g.).

EXAMPLES 8–11

Methyl acrylate (14.5 g.) was added to 5-acetyl-2-aminobenzimidazole (26.6 g.) in ethanol (200 ml.). The solution was heated under reflux for 20 hours and the reaction mixture allowed to cool. The crystalline precipitate was separated by filtration and washed with ethanol and ether to give a solid (31.7 g.) which was recrystallised from dimethylformamide (DMF) to give a 1:1 mixture of 7- and 8-acetyl-3,4-dihydropyrimido[1,2-a]benzimidazol-2(1H)-one (Example 8) (29.5 g.); m.p., >330° C., (microanalysis: C$_{12}$H$_{11}$N$_3$O$_2$ requires C, 62.9; H, 4.8; N, 18.3%; found C, 62.8; H, 4.7; N, 18.4%; NMR spectrum (+TFA) showed two equal triplets $\delta$ 4.50, 4.55 corresponding to the proton at C4.

In a similar manner, but using the appropriate 2-aminobenzimidazole of formula VIII and methyl acrylate, there were obtained the following compounds of the formula IX:

| Example No. | Reaction Time (hr.) | Substituent on ring A | Yield % | m.p. (°C.) | microanalysis |
|---|---|---|---|---|---|
| 9 | 72 | 7-PhCO— or 8-PhCO— Note A | 52 | 305–315 | found: C, 70.1; H, 4.4; N, 14.4%; C$_{17}$H$_{13}$N$_3$O$_2$ requires C, 70.1, H, 4.5; N, 14.4% |
| 10 | 24 | 7-CN or 8-CN Note B | 38 | >320 | found: C, 62.3; H, 3.9; N, 26.4%; C$_{11}$H$_8$N$_4$O requires C, 62.3; H, 3.8; N, 26.4% |
| 11 | 24 | 7,8-methylenedioxy | 60 | >330 | found: C, 57.0; H, 3.8; N, 18.0%; C$_{11}$H$_9$N$_3$O$_3$ requires C, 57.1; H, 3.9; N, 18.2% |

Note A: isolated as a 1:1 mixture of 7- and 8-benzoyl-3,4-dihydropyrimido[1,2-a]benzimidazol-2(1H)-one; NMR:- $\delta$2.90 (t, 2 protons, C3-H2); 4.30 (t, 2 protons, C4-H$_2$); 7.4–7.8 (complex, 8 aromatic protons).
Note B: shown to be a 1:1 mixture of 7- and 8-cyano-3,4-dihydropyrimido[1,2-a]benzimidazol-2(1H)-one by NMR i.e. 2 equal singlets at $\delta$7.98 (C9-H, 8-CN isomer) and $\delta$7.89 (C6-H, 7-CN isomer).

Those of the starting materials of formula VIII which are new were obtained as follows:

(a) 5-Acetyl-2-aminobenzimidazole (for Example 9)

4-Amino-3-nitroacetophenone (38.7 g.) in ethyl acetate (1 l.) containing hydroquinone (10 mg.) was hydrogenated over 10% palladium-on-charcoal at room temperature and atmospheric pressure, until hydrogen uptake ceased. The catalyst was removed by filtration and the filtrate was evaporated. The solid product was stirred in water (100 ml.), separated and dried to give 3,4-diaminoacetophenone (28.6 g.) m.p. 131°–4° C.

Cyanogen bromide (20 g.) in water (400 ml.) was added to a stirred suspension of 3,4-diaminoacetophenone (25 g.) in methanol (400 ml.). The solution was kept at room temperature for 16 hours and then evaporated. The residue was dissolved in water and the solution was basified with an excess of saturated sodium carbonate solution. The suspension obtained was stirred for 1 hour, filtered, washed with water and dried to give 5-acetyl-2-aminobenzimidazole (26.6 g.), m.p. 228°–234° C.

(b) 2-Amino-5-cyanobenzimidazole (for Example 11)

Using a similar procedure to that described above, there was obtained, from 3,4-diaminobenzonitrile (7.8 g.) and cyanogen bromide (6.9 g.), 2-amino-5-cyanobenzimidazole as a solid (8.1 g.), m.p. 228°–233° C., and of satisfactory purity.

(c) 2-Amino-5,6-methylenedioxybenzimidazole (for Example 12)

Cyanogen bromide (3.4 g.) in water (60 ml.) was added to 3,4-methylenedioxy-o-phenylenediamine (3.8 g.) in ethanol (60 ml.) to give 2-amino-5,6-methylenedioxybenzimidazole (4.4 g.) m.p. 230°–243° C.

EXAMPLE 12

5-Acetyl-2-amino-1-(2-cyanoethyl)-benzimidazole (1.2 g.) was heated under reflux in ethanol (20 ml.) containing potassium hydroxide (1.2 g.) for 2 hours. The mixture was concentrated to low volume and water (20 ml.) was added. The solution was acidified to pH 5 with acetic acid and kept at 4° C. for 16 hours. The solid which formed was separated by filtration and dried by azeotropic distillation of a suspension in toluene to give 5-acetyl-2-amino-1-(2-carboxyethyl)benzimidazole (0.85 g.) which was not characterised, but was heated at 250° C. for 5 minutes to give a tar, which was extracted with 3 N-hydrochloric acid (3×10 ml.). The acid extracts were basified by addition of an excess of saturated sodium carbonate solution to give a brown solid, which was washed with DMF, acetone and then ether to give 8-acetyl-3,4-dihydropyrimido-[1,2-a]benzimidazol-2(1H)-one (0.22 g.), m.p. >320° C.; microanalysis: $C_{12}H_{11}N_3O_2$. $\frac{3}{4}$ $H_2O$ requires C, 59.4; H, 5.1; N, 17.3%; found C, 59.3; H, 4.7; N, 17.0%; NMR: δ 2.55 (S, 3 protons $COCH_3$), 3.0 (t, 2-protons, $C_3$-$\underline{H}_2$), 4.42 (t, 2 protons, $C_4$-$H_2$), 7.64 (d, 1 proton, $C_6$-$\underline{H}$), 7.95 (m, 1 proton, $C_7$-$\underline{H}$) and 8.05 (s, 1 proton $C_9$-$\underline{H}$).

The 5-acetyl-2-amino-1-(2-cyanoethyl)benzimidazole used as starting material was obtained in the following manner:

4-Amino-3-nitroacetophenone (10.0 g.), suspended in dioxan (25 ml.) was treated, with stirring with choline hydrate (0.5 ml. of 45% solution in methanol) at 32° C. Acrylonitrile (3.3 g.) was added in portions at 32° C. and the temperature was raised to 50° C. and maintained at that temperature for 90 minutes. Ether (50 ml.) was added to the thick reaction mixture. The solid was then separated by filtration to give 4-(2-cyanoethylamino)-3-nitroacetophenone, (11.2 g.), m.p. 138°–142° C.

A solution of 4-(2-cyanoethylamino)-3-nitroacetophenone (10.2 g.) in ethanol (200 ml.) was hydrogenated over 10% w/w palladium-on-charcoal (1 g.). 3N-Hydrochloric acid (50 ml.) was added to the mixture after uptake of hydrogen was complete. The mixture was then shaken, and separated by filtration. The filtrate was basified by addition of an excess of aqueous sodium carbonate solution. The precipitated solid obtained was separated by filtration, washed with water and then with acetone to give 4-(2-cyanoethylamino)-3-aminoacetophenone (6.2 g.), m.p. 170°–3° C., which was then dissolved in methanol (200 ml.) and treated with cyanogen bromide (3.5 g.). The mixture was stirred at room temperature overnight and then water (200 ml.) and sodium carbonate solution was added to pH 7 to give 5-acetyl-2-amino-1-(2-cyanoethyl)benzimidazole (3.6 g.) whose IR spectrum shows bands at ν 3460, 3340, 2260, 1650, 1610 $cm^{-1}$.

EXAMPLE 13

A 1:1 mixture of 7- or 8-acetyl-3,4-dihydropyrimido-[1,2-a]benzimidazol-2(1H)-one (1.5 g.) was dissolved in boiling DMF (100 ml.) and the solution seeded with a pure sample of 8-acetyl-3,4-dihydropyrimido[1,2-a]benzimidazol-2(1H)-one (from Example 12). The solution was allowed to cool to room temperature whereupon two distinct crystal forms were deposited i.e., light crystals which were shown to be rich in the 8-acetyl isomer, and heavy crystals which were shown to be rich in the 7-acetyl isomer, in each case by NMR spectroscopic comparison with the authentic 8-acetyl isomer. The two crystalline forms were separated by swirling the mixture and them removing the light crystals with the mother liquors by decantation. In this way a sample (A) (0.05 g.) containing 80% 7-acetyl isomer was obtained. This sample (A) was then used to seed a crystallising solution of a fresh sample of the 1:1 mixture of 7- and 8-isomers (4.0 g.) in boiling DMF (300 ml.), which then gave crops of light crystals (B) and heavy crystals (C), which were separated by decantation. The light crystals (B) were then heated with their mother liquors, and the hot solution seeded with a sample of the pure 8-acetyl isomer, so that a further crop of light crystals (D) and heavy crystals (E) were obtained. The light crystals (D) were then again redissolved in their mother liquors and the solution again seeded with pure 8-isomer, so that a yet further crop of light crystals (F) and heavy crystals (G) was obtained.

The heavy crystal crops C, E and G were combined and recrystallised twice (without seeding) from boiling DMF to give 7-acetyl-3,4-dihydropyrimido[1,2-a]benzimidazol-2(1H)-one (0.65 g.), m.p. >320° C.; microanalysis, found C, 62.4; H, 4.8; N, 17.9%; $C_{12}H_{11}N_3O_2$ requires C, 62.9; H, 4.8, N, 18.3%; NMR (in TFA solution):

δ 2.87 (s, 3 protons, $COC\underline{H}_3$), 3.42 (t, 2 protons, $C_3\underline{H}_3$),
4.75 (t, 2 protons, $C_4$-$\underline{H}_2$), 7.84 (d, 1 proton, $C9$-$\underline{H}$),
8.32 (d, 1 proton, $C8$-$\underline{H}$), 8.40 (s, 1 proton, $C6$-$\underline{H}$).

Similarly recrystallisation of light crystal crop F from boiling DMF gave a sample of 8-acetyl-3,4-dihydropyrimido-[1,2-a]benzimidazol-2(1H)-one having identical physical properties to those described in Example 12.

EXAMPLE 14

Sodim borohydride (0.4 g.) was added to a 1:1 mixture of 7- and 8-acetyl-3,4-dihydropyrimido[1,2-a]benzimidazol-2(1H)-one (2.3 g.) in DMF (10 ml.). The mixture was heated at 100° C. for 30 minutes, and then evaporated. Water (100 ml.) was then added and the solution was neutralised with acetic acid, and then heated to 100° C. for 30 minutes. The suspension obtained was then cooled to 5° C. and the solid separated by filtration, washed with cold water, acetone and then ether to give a 1:1 mixture of 7- and 8-(1-hydroxyethyl)-3,4-dihydropyrimido[1,2-a]benzimidazol-2(1H)-one (1.4 g.). This material was purified by solution in boiling methanol (100 ml.) followed by concentration to 30 ml. to give 8-(1-hydroxyethyl)pyrimidol[1,2-a]benzimidazol-2(1H)-one (0.4 g.) m.p. 270°–8° C.; microanalysis, $C_{12}H_{13}N_3O_2$ requires: C, 62.3; H, 5.6; N, 18.2%; found: C, 6.21; H, 5.6; N, 17.9%. The NMR spectrum shows a signal at δ 7.38 (s, 1 proton, $C9$-H).

The mother liquors from the above crystallisation slowly deposited a mixture of 8- and 7-(1-hydroxyethyl)-3,4-dihydropyrimido[1,2-a]benzimidazol-2(1H)-one (0.74 g.), m.p. 247°–252° C. This mixture was shown by NMR spectroscopy to contain 60 parts of the 8-isomer to 40 parts of the 7-isomer by comparing the integration of their respective signals for C4-H at δ 4.24(t) and 4.23(t) respectively.

EXAMPLES 15–18

Using a generally similar procedure to that described in Example 8 the following compounds of formula I were obtained from the appropriate 2-aminobenzimidazole and methyl acrylate (MA) in yields of 70–90%:

(Example 15)—a 1:1 mixture of 7- and 8-butyryl-3,4-dihydropyrimido[1,2-a]benzimidazol-2(1H)-one; obtained as a solid, m.p. 287°–300° C., [crystallised from dimethyl formamide (DMF)]; microanalysis; $C_{14}H_{15}N_3O_2$ requires: C, 65.4; H, 5.8; N, 16.3%; found: C, 65.0; H, 5.9; N, 16.2%; NMR (TFA) shows 2 equal triplets (C4-H$_2$) at δ4.66 and 4.70; by heating 5-butyryl-2-aminobenzimidazole with MA in ethanol under reflux for 72 hours;

(Example 16)—1:1 mixture of 7- and 8-(p-chlorobenzoyl)-3,4-dihydropyrimido[1,2-a]benzimidazol-2(1H)-one; obtained as a solid, m.p. 315°–325° C.; microanalysis; $C_{16}H_{12}N_3OCl$ requires: C, 62.7; H, 3.7; N, 12.9; Cl, 10.9%; found: C, 62.2; H, 3.5; N, 12.4; Cl, 10.8%; NMR (TFA): δ, 3.30 (t, 2 protons, C3-H$_2$); 4.60 (t, 2 protons, C4-H$_2$); 7.71 (s, 1 proton, C6-H); 7.86 (s, 1 proton, C9-H); by heating 5-(p-chlorobenzoyl)-2-aminobenzimidazole with MA in methanol under reflux for 16 hours;

(Example 17)—7,8-dichloro-3,4-dihydropyrimido[1,2-a]benzimidazol-2(1H)-one; obtained as a solid, m.p. >345° C.; microanalysis, $C_{10}H_7N_3OCl_2$ requires: C, 46.9; H, 2.7; N, 16.4%; found: C, 46.9; H, 2.8; N, 16.4%; by heating 5,6-dichloro-2-aminobenzimidazole with MA in ethanol under reflux for 72 hours;

(Example 18)—a 49:1 mixture of 8,9- and 6,7-dimethyl-3,4-dihydropyrimido[1,2-a]benzimidazol-2(1H)-one; obtained as a solid, m.p. 240°–244° C. (recrystallised from ethanol); microanalysis, $C_{12}H_{13}N_3O \cdot \frac{1}{4}H_2O$ requires: C, 65.5; H, 6.2; N, 19.1%; found: C, 65.5; H, 6.2; N, 19.0%; NMR (TFA) shows two triplets at δ4.42 (C4-H$_2$ of 8,9-isomer) and 4.10 (C4-H$_2$ of 6,7-isomer) in the ratio of 49:1 respectively; by treating 4,5-dimethyl-2-aminobenzimidazole with MA in ethanol at room temperature.

The necessary 2-aminobenzimidazole starting materials of formula VIII were obtained in a similar manner to that described in Example 8 for 5-acetyl-2-aminobenzimidazole-2(1H)-one, but starting with the appropriate 2-nitroaniline:

| Starting Material for Example | Substituent on ring A | Yield % | m.p.°C. |
|---|---|---|---|
| 15 | 5-butyryl | 59 | 235–240 |
| 16 | 5-(p-chlorobenzoyl) | 63 | 235–240 |
| 17 | 5,6-dichloro | 55 | 259–262 |
| 18 | 4,5-dimethyl | 26 | 216–220 |

EXAMPLE 19

2-Amino-5-benzoylbenzimidazole (2.37 g.) and methyl methacrylate (1.1 g.) were heated under reflux in ethanol (20 ml.) for 72 hours. More methyl methacrylate (0.8 g.) was added and the reaction mixture was heated for a further 6 days. The mixture was cooled to room temperature and the solid which deposited was collected by filtration and washed with ethanol and ether to give a 1:1 mixture of 7- and 8-benzoyl-3,4-dihydro-3-methylpyrimido[1,2-a]benzimidazol-2(1H)-one (1.4 g.), m.p. 296°–321° C.; microanalysis, $C_{18}H_{16}N_3O_2$ requires: C, 70.8; H, 4.9; N, 13.8%; found: C, 70.4; H, 4.9; N, 13.6%; NMR (TFA) shows two doublets (C3-H) at δ4.84 and 4.93 of equal intensity.

EXAMPLE 20

2-Amino-5-benzoylbenzimidazole (2.4 g.) and ethyl crotonate (1.25 g.) were heated under reflux in butan-1-ol (20 ml.) for 4 days. On cooling the mixture a solid separated which was recrystallized from methanol to give a solid (0.5 g.) which was shown by NMR to be a 2:1 mixture of 7- and 8-benzoyl-3,4-dihydro-4-methylpyrimido[1,2-a]benzimidazol-2(1H)-one. Evaporation of the liquors of crystallisation gave a 1:1 mixture of 7- and 8-benzoyl-3,4-dihydro-4-methylpyrimido[1,2-a]benzimidazol-2(1H)-one (1.35 g.), m.p. 250°–270° C.; microanalysis, $C_{18}H_{15}N_3O_2$ requires: C, 70.8; H, 4.9; N, 13.8%; found: C, 71.0; H, 5.2; N, 13.9%; NMR shows two doublets (C4-CH$_3$) at δ1.25 and 1.31 of equal intensity.

EXAMPLE 21

A solution of 3-(2-amino-5-benzoylbenzimidazol-1-yl)-propionic acid (6.1 g.) in methanol (30 ml.) was treated with a saturated solution (30 ml.) of hydrogen chloride in methanol. The mixture was left at room temperature for 16 hours and then evaporated. The residue was dissolved in water. The solution obtained was adjusted to pH 8.5 with aqueous sodium bicarbonate solution and then extracted with ethyl acetate (3×50 ml.). The extracts were dried (MgSO$_4$) and evaporated to give methyl 3-(2-amino-5-benzoylbenzimidazol-1-yl)propionate as an oil. This oil was dissolved in methanol (60 ml.) and the solution heated at reflux for 5 hours. The solid which precipitated was collected and washed successively with methanol, acetone and then ether to give 8-benzoyl-3,4-dihydropyrimido[1,2-a]-benzimidazol-2(1H)-one (3.4 g.), m.p. 323°–330° C., microanalysis, $C_{17}H_{13}N_3O_2$ requires: C, 70.1; H, 4.5; N, 14.4% found: C, 69.9; H, 4.4; N, 14.0%.

The starting material was obtained as follows:

4-Chloro-3-nitrobenzophenone (10 g.) was added to a mixture of 3-aminopropionic acid (β-alanine) (10.1 g.) and sodium hydrogen carbonate (9.6 g.) in 2-methoxyethanol (100 ml.) which was then heated under reflux for 4 hours. The mixture was cooled, poured into ice-water (250 ml.) and brought to pH 3 by addition of concentrated hydrochloric acid. The solid obtained was filtered, washed with water and air-dried to give 3-(4-benzoyl-2-nitroanilino)propionic acid (12.1 g), m.p. 170°–5° C.

This acid (10 g.) was dissolved in ethanol (100 ml.) and hydrogenated in the presence of 10% w/w palladium-carbon (0.6 g.) until uptake of hydrogen ceased. Water (100 ml.) and cyanogen bromide (3.72 g.) was then added. After 16 hours at room temperature the mixture was evaporated. Water (50 ml.) was added to the residue. The aqueous phase was separated from tarry material by decantation, and adjusted to pH 4 with concentrated aqueous ammonia to give 3-(2-amino-5- benzoylbenzimidazol-1-yl)propionic acid as a solid (6.1 g.), m.p. 325°–330° C.

EXAMPLE 22

Using a similar procedure to that described in Example 21, 8-cyano-3,4-dihydropyrimido[1,2-a]benzimidazol-2(1H)-one was obtained as a solid in essentially quantitative yield m.p. >340° C., (microanalysis, $C_{11}H_8N_4O$ requires: C, 62.3; H, 3.8; N, 26.4%; found C, 61.8; H, 3.7; N, 26.0;) by thermal cyclisation of the methyl ester of 3-(5-cyano-2-aminobenzimidazol-1-yl)propionic acid, itself obtained as an oil of satisfactory purity by esterification of the propionic acid with methanolic hydrogen chloride.

The starting 3-(5-cyano-2-aminobenzimidazol-1-yl)-propionic acid was prepared in a similar manner to the analogous starting material in Example 21 as a solid, m.p. >320° C., of satisfactory purity, from 3-(4-cyano-2-nitroanilino)propionic acid, itself obtained as a solid, m.p. 200°–205° C., by reaction of β-alanine with 4-chloro-3-nitrobenzonitrile.

EXAMPLE 23

Using a similar procedure to that described in Example 1, there was obtained from methyl acrylate (2.8 g.) and 2-amino-5-ethylthiobenzimidazole (6.3 g.), a 1:1 mixture (3.1 g.) of 7- and 8-ethylthio-3,4-dihydropyrimido[1,2-a]benzimidazol-2(1H)-one, m.p. 185°–186° C.; NMR shows two triplets ($C_4$-$H_2$) at δ 4.22 and 4.23 of equal intensity.

The necessary, starting benzimidazole was obtained as follows:

Sodium (2.76 g.) was added to dry 2-methoxyethanol (75 ml.) and the solution was cooled to 0°–5° C. Ethanethiol (8.72 g.) in 2-methoxyethanol (10 ml.) was added during 5 minutes and the subsequent solution was stirred at 0°–5° C. for 10 minutes and then added in portions to a solution of 5-chloro-2-nitro acetanilide (21.5 g.) in boiling 2-methoxyethanol (150 ml.) during 10 minutes. After 3 hours the mixture was cooled and poured into water (1 l.). The mixture was stirred and cooled to 10° C. The solid which formed was collected by filtration, washed with water, and recrystallized from ethanol to give 5-ethylthio-2-nitroaniline (16.4 g.), m.p. 75°–6° C.

A solution of 5-ethylthio-2-nitrolaniline (8.2 g.) in ethanol (100 ml.) was hydrogenated over 10% w/w palladium carbon (0.8 g.). Water (75 ml.) was added to the mixture, maintained under an atmosphere of nitrogen, followed by cyanogen bromide (8.7 g.) over a period of 10 minutes. After 3 days stirring at room temperature, the mixture was filtered and the filtrate was concentrated to a low volume. Water (75 ml.) was added followed by 10% w/v sodium carbonate solution to adjust the pH to 8. The solid which precipitated was collected by filtration, washed with water, air dried and then triturated with acetone to give 2-amino-5-ethylthiobenzimidazole (6.3 g.), having characteristic absorption bands at ν3440, 3360, 1660, 1645 and 1560 cm$^{-1}$, in the IR spectrum.

EXAMPLE 24 m-Chloroperbenzoic acid (1.03 g.) was added to a solution of a 1:1 mixture of 7- and 8-ethylthio-3,4-dihydropyrimido[1,2-a]benzimidazol-2(1H)-one (1.23 g.) in methanol (150 ml.) at 0°–5° C. After 30 minutes, the mixture was evaporated to low volume. The solid obtained was separated by filtration and washed with methanol and ether to give a 1:1 mixture of 7- and 8-ethylsulphinyl-3,4-dihydropyrimido[1,2-a]benzimidazol-2(1H)-one as its hemihydrate (0.95 g.), m.p. 226°–230° C.; microanalysis, $C_{12}H_{13}N_3SO_2.\frac{1}{2}H_2O$ requires: C, 52.9; H, 5.1; N, 15.4%; found: C, 53.2; H, 5.0; N, 15.4%; NMR (TFA): δ1.38 (t, 3 protons, $CH_3$); 3.38 (complex, 4 protons, $C3$-$H_2$ and $CH_2SO$); 4.71 [t, 2 protons, $C4$-$H_2$ (7 isomer)]; 4.80 [t, 2 protons, $C4$-$H_2$ (8 isomer)]; 7.90 (complex, 2 aromatic protons); 8.3 (s, 1 aromatic proton).

EXAMPLE 25

2-Amino-6,8-dimethylbenzimidazole (2.6 g.) and methyl acrylate (1.5 g.) were stirred in ethanol (25 ml.), at 25° C. for 5 days. The solid which formed was collected by filtration and washed with ethanol, acetone and ether to give a 9:1 mixture (2.1 g.) of 7,9- and 6,8-dimethyl-3,4-dihydropyrimido[1,2-a]benzimidazol-2(1H)-one, m.p. 326°–32° C.; microanalysis, $C_{12}H_{13}N_3O$ requires: C, 67.0; H, 6.0; N, 19.5%; found: C, 66.7; H, 6.1; N, 19.5%; NMR shows 2 triplets ($C_4$-$H_2$) at δ4.01 (7,9-isomer) and 4.32 (6,8-isomer) in the ratio of 9:1 respectively.

EXAMPLE 26

Methyl acrylate (6.1 g.) was added to a solution of 2-amino-5,6-dimethoxybenzimidazole (12.2 g.) in methanol (70 ml.) and the mixture was stirred for 90 hours. The crystalline precipitate was separated by filtration and washed with ethanol and then ether to give 7,8-dimethoxy-3,4-dihydropyrimido[1,2-a]-benzimidazol-2(1H)-one (10.3 g.), m.p. 264°–5° C.; microanalysis, $C_{12}H_{13}N_3O_3$ requires: C, 58.3; H, 5.3; N, 17.0%; found: C, 58.0; H, 5.2; N, 16.8%; NMR: δ2.82 (t, 2 protons, $C3$-$H_2$); 3.72 (s, 3 protons, $CH_3O$); 3.76 (s, 3 protons, $CH_3O$); 4.15 (t, protons $C_4$-$H_2$); 7.00 (s, 1 proton, $C6$-$H$); 7.04 (s, 1 proton, $C9$-$H$).

EXAMPLE 27

2-Amino-6,8-dimethylbezimidazole (9.3 g.) and methyl acrylate (5.3 g.) were heated together in methanol (70 ml.), under reflux for 4 hours. The crystalline precipitate which formed was filtered from the hot solution and washed with methanol to give a mixture of 7,9- and 6,8-dimethyl-3,4-dihydro pyrimido[1,2-a]benzimidazole-2(1H)one (2.4 g.), m.p. 325°–7° C., containing 98% of the 7,9-isomer as shown in NMR by comparison of the triplets for $C4$-$H_2$ at δ4.01 (7,9-isomer) and 4.32 (6,8-isomer).

EXAMPLE 28

A mixture of micro-crystalline cellulose (196 parts by weight) and finely divided 8-acetyl-3,4-dihydropyrimido[1,2-a]-benzimidazol-2(1H)-one (200 parts by weight) was sieved through a 30 mesh screen. Magnesium stearate (60 mesh particle size) (4 parts by weight) was added and, after thorough mixing the mixture was compressed into tablets, weighing 400 mg. and containing 200 mg. of active ingredient, which may be administered to man for therapeutic purposes.

In a similar manner tablets containing 150, 100 or 50 mg. of active ingredient may be obtained.

The above active ingredient may be replace by any compound of formula I described in any of Examples 1–11 or 13–27.

What we claim is:

1. A pyrimido[1,2-a]benzimidazole derivative of the formula:

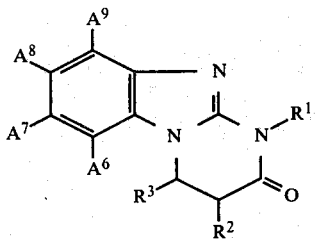

wherein $R^1$ is hydrogen, or a $C_{1-6}$-alkyl radical; $R^2$ and $R^3$, which may be the same or different, are hydrogen or $C_{1-6}$-alkyl radicals; one or two of $A^6$, $A^7$, $A^8$ and $A^9$, which may be the same or different, are halogen atoms, $C_{1-6}$-alkyl, $C_{1-6}$-alkoxy, $C_{2-6}$-alkanoyl, 1-(hydroxy)-$C_{1-6}$-alkyl, $C_{1-6}$-alkylthio, $C_{1-6}$-alkylsulphinyl or cyano radicals, or benzoyl radicals optionally substituted by a halogen atom, a $C_{1-6}$-alkoxy or $C_{1-6}$-alkyl radical, and the remainder of $A^6$, $A^7$, $A^8$ and $A^9$ are hydrogen; or an adjacent pair of $A^6$, $A^7$, $A^8$ and $A^9$ together constitute a $C_{1-6}$-alkylenedioxy diradical, and the remainder of $A^6$, $A^7$, $A^8$ and $A^9$ is hydrogen; provided that when only one of $A^6$, $A^7$, $A^8$ and $A^9$ is a halogen atom, $C_{1-6}$-alkyl or $C_{1-6}$-alkoxy radical one of the remainder of $A^6$, $A^7$, $A^8$ and $A^9$ is other than hydrogen.

2. A compound as claimed in claim 1 wherein $R^1$ is hydrogen or a methyl or ethyl radical; $R^2$ and $R^3$, which may be the same or different, are hydrogen or methyl or ethyl radicals; one or two of $A^6$, $A^7$, $A^8$ and $A^9$, which may be the same or different, are fluorine, chlorine or bromine atoms, methyl, ethyl, propyl, methoxy, ethoxy, i-propoxy, acetyl, propionyl, butyryl, hyroxymethyl, 1-hydroxyethyl, 1-hydroxypropyl, 1-hydroxybutyl, methylthio, ethylthio, methylsulphinyl, ethylsulphinyl or cyano radicals, or benzoyl radicals optionally substituted by a fluorine, chlorine or bromine atom, or by a methyl or methoxy radical and the remainder of $A^6$, $A^7$, $A^8$ and $A^9$ are hydrogen; or an adjacent pair of $A^6$, $A^7$, $A^8$ and $A^9$ together constitute a methylenedioxy or isopropylidenedioxy radical, and the remainder is of $A^6$, $A^7$, $A^8$ and $A^9$ is hydrogen, or is an atom or radical as defined above.

3. A compound as claimed in claim 1 wherein two of $A^6$, $A^7$, $A^8$ and $A^9$ constitute a 6,7-, 7,8-, 8,9- or 6,9-dimethyl radical, a 7,8-dichloro, 7-chloro-8-methyl, 7-methyl-8-chloro, 7,8-dimethoxy, 7,8-diisopropoxy or a 7,8-methylenedioxy radical, and the remainder of $A^6$, $A^7$, $A^8$ and $A^9$ are hydrogen; or wherein one of $A^6$, $A^7$, $A^8$ and $A^9$ is a 7- or 8-acetyl, -butyryl, -benzoyl, -(p-chloro)benzoyl, -methylthio, -ethylthio, -ethylsulphinyl, -cyano or -[1-(hydroxy)ethyl] radical, and the remainder of $A^6$, $A^7$, $A^8$ and $A^9$ are hydrogen.

4. A compound as claimed in claim 1 wherein $R^1$ is hydrogen, $R^2$ and $R^3$, which may be the same or different, are hydrogen or methyl radicals, at least two of $A^6$, $A^7$, $A^8$ and $A^9$ are hydrogen, and the remainder of $A^6$, $A^7$, $A^8$ and $A^9$ have any of the values other than hydrogen defined in claim 1.

5. A compound as claimed in claim 1, wherein $R^1$ is hydrogen, $R^2$ and $R^3$, which may be the same or different, are hydrogen or methyl radicals, $A^7$ and one of $A^6$, $A^8$ and $A^9$ have any of the values other than hydrogen defined in claim 1 and the remainder of $A^6$, $A^8$ and $A^9$ is hydrogen.

6. A compound as claimed in claim 1, wherein $R^1$ is hydrogen, $R^2$ and $R^3$, which may be the same or different, are hydrogen or methyl radicals, $A^8$ and one of $A^6$, $A^7$ and $A^9$ have any of the values other than hydrogen defined in claim 1, and the remainder of $A^6$, $A^7$ and $A^9$ are hydrogen.

7. A compound as claimed in claim 1 wherein $R^1$ is hydrogen, $R^2$ and $R^3$, which may be the same or different, are hydrogen or methyl radicals, $A^7$ and/or $A^8$ have any of the values other than hydrogen defined in claim 1, and the remainder of $A^6$, $A^7$, and $A^8$ and $A^9$ are hydrogen.

8. A compound as claimed in claim 1 wherein $A^7$ or $A^8$ is a cyano, acetyl, 1-(hydroxy)ethyl or benzoyl radical.

9. A compound as claimed in claim 1 wherein $A^7$ and $A^8$ together constitute a methylenedioxy diradical, or are methoxy, ethoxy or isopropoxy radicals.

10. The compounds 7-acetyl-, 8-acetyl-, 7-benzoyl-, 8-benzoyl-, 7-cyano-, 8-cyano-, 7,8-di-isopropoxy- and 7,8-methylenedioxy-3,4-dihydropyrimido[1,2-a]benzimidazol-2-(1H)-one, and 7-benzoyl-, and 8-benzoyl-4-methyl-3,4-dihydropyrimido-[1,2-a]benzimidazol-2(1H)-one.

11. A pharmaceutical composition for use in inhibiting the aggregation of blood platelets which comprises an effective amount of a compound of formula I as claimed in claim 1 together with a pharmaceutically acceptable diluent or carrier.

12. A composition as claimed in claim 11 which is in the form of a tablet, capsule, aqueous or oily suspension.

13. A method of inhibiting the aggregation of blood platelets in an animal requiring such treatment which comprises administering to said animal an effective amount of a compound of formula I as claimed in claim 1.

14. A method of stabilising an in vitro preparation of blood platelets which comprises adding to said preparation a blood platelet aggregation inhibitory amount of a compound of formula I as claimed in claim 1.

15. The compound 8-cyano-3,4-dihydropyrimido[1,2-a]benzimidazol-2(1H)-one.

* * * * *